United States Patent [19]

LaBombard

[11] Patent Number: 5,042,475
[45] Date of Patent: Aug. 27, 1991

[54] HINGED TRACHEOSTOMY TUBE OBTURATOR

[75] Inventor: Denis LaBombard, Georgetown, Mass.

[73] Assignee: Portex, Inc., Wilmington, Mass.

[21] Appl. No.: 492,406

[22] Filed: Mar. 8, 1990

Related U.S. Application Data

[63] Continuation of Ser. No. 252,099, Sep. 30, 1988, abandoned.

[51] Int. Cl.$^5$ .............................................. A61M 16/00
[52] U.S. Cl. ............................. 128/207.14; 128/200.26
[58] Field of Search ...................... 128/200.26, 207.14, 128/207.15; 606/108; 600/12

[56] References Cited

U.S. PATENT DOCUMENTS

| | | | |
|---|---|---|---|
| 3,443,564 | 5/1969 | Oehmig | 128/207.14 |
| 3,625,200 | 12/1971 | Muller | 128/772 |
| 3,674,014 | 7/1972 | Tillander | 128/657 |
| 3,794,041 | 2/1974 | Frei et al. | 128/348.1 |
| 4,111,190 | 9/1978 | Plumridge | 128/348.1 |
| 4,231,365 | 11/1980 | Scarberry | 128/207.15 |
| 4,244,362 | 1/1981 | Anderson | 128/200.26 |
| 4,278,081 | 7/1981 | Jones | 128/207.15 |
| 4,762,130 | 8/1988 | Fogarty et al. | 128/348.1 |

FOREIGN PATENT DOCUMENTS

| | | | |
|---|---|---|---|
| 0138089 | 4/1985 | European Pat. Off. | 128/343 |
| 1024093 | 6/1983 | U.S.S.R. | 128/343 |
| 1446907 | 8/1976 | United Kingdom . | |
| 2169515 | 7/1986 | United Kingdom | 128/207.14 |

*Primary Examiner*—Aaron J. Lewis
*Attorney, Agent, or Firm*—Pollock, Vande Sande & Priddy

[57] ABSTRACT

A plastic obturator for use in intubating tracheostomy tubes, particularly including a non-constant radius cannula, which is made of a single-piece plastic flexible member having a flexible shaft including a substantially flat strip member and a plurality of segments extending substantially perpendicular to the strip member. The strip member forms a plurality of hinge members which alternate with this plurality of segments. The shaft means includes a distal and a proximal end. A holding means is formed at the proximal end of the shaft means and a tip member is provided at the distal end of the shaft means having a bullet-like conical shape.

8 Claims, 2 Drawing Sheets

HINGED TRACHEOSTOMY TUBE OBTURATOR

This application is a continuation of Ser. No. 252,099, filed on Sept. 30, 1988, now abandoned.

FIELD OF THE INVENTION

The present invention relates to tracheostomy tube devices and more particularly to an improvement in guiding devices such as obturators that are used to assist in the insertion of a tracheostomy tube into a patient's trachea.

The obturator of the present invention is particularly designed for use with a tracheostomy tube which includes a non-constant radius cannula as a part of its configuration.

BACKGROUND OF THE INVENTION

Tracheostomy tubes are widely used to supply air to the lungs of unconscious patients such as injured persons and patients undergoing surgery.

In order for the tracheostomy tube to function as intended it must be properly applied to the trachea so that air can be directed through the tube and into the trachea. However, proper insertion of the tube, represents a very difficult task and it is possible during the insertion procedure to miss the surgically prepared opening in the trachea and misguide the tracheostomy tube device into the surrounding tissue. Failure to properly insert the tracheal tube can cause serious problems and incur dangerous consequences for the patient. Otolaryngologists, Thoracic Surgeons, General Surgeons and other clinical professionals may experience difficulties in performing intubation procedures. To assist the physician, a variety of guides such as stylets or obturators are available to clinicians to guide and to assist the placement of such tubes in the patient's trachea.

Obturators are used to guide metal or polymeric tracheostomy tubes such as described, for example, in U.S. Pat. Nos. 3,088,466 and 3,659,612 to Shiley et al. The characteristic common feature of these tubes is a constant radius design of the cannula portion. A constant radius cannula is defined herein as a cannula having a continuous curvature between its proximal and distal ends.

It is important in the intubation procedure that the obturator be not only be easily insertable into the cannula, but also easily and safely removable after the intubating has been completed.

The removal of the obturator used with tracheostomy tubes having constant radius cannula does not present significant problems as the obturator can be easily pulled along the radius of curvature for easy frictionless removal.

However, many flexible tracheostomy tubes used nowadays are designed to include a non-constant radius cannula. Typically such a tracheostomy tube has at least two substantially straight cannula sections and a curved section located therebetween. The arc of the curve may be designed as forming a right angle or approaching a right angle. The straight sections may be of considerable length. The withdrawal of the obturator from the non-constant radius cannula presents a more difficult task.

U.S. Pat. No. 4,471,776 to Cox describes an example of a tracheostomy tube including an obturator with an adjustable shape. This obturator includes a mealable shaft which allows for the obturator placed inside the tube to be bent together with the tube to a desired curved configuration. However, it is difficult to remove the obturator from the tracheostomy tube since the forces which maintain the curved geometry of the tube and the obturator have to be overcome.

Other types of flexible guiding devices available on the market are so-called "steerable" wire guide devices which bend to a selected fixed constant curvature. Such guiding stylets inserted into the catheter/cannula are designed to impact the curvature to the catheter/cannula. The wire-type guiding devices are most commonly employed with medical devices having an extremely long length as compared to their diameter which is usually very small. The spring-like functions of such small diameter guidewires would be difficult to overcome when such mechanisms are applied to the typical geometry of a tracheostomy or endotracheal tube.

For accomplishing a proper intubation, it is very important that the cannula maintains its shape and does not become occluded or distorted, such that an airway passway is maintained clear through the intubated cannula during and after the intubation procedure.

There is a significant need in the art for an obturator suitable for use with tracheostomy tubes, particularly those including a non-constant radius cannula, which would eliminate disadvantages of the prior art. There does not exist a highly flexible, plastic, single-piece, easily insertable and safely removable guiding device especially suitable for tracheostomy tubes having non-constant radius cannula.

There is a need for an obturator which would substantially prevent tracheostomy tube occlusion or collapse during the intubation and additional distortion of the device once the tube is in place in the trachea, increasing the patient's safety and comfort.

SUMMARY OF THE INVENTION

It is the primary object of the present invention to provide an improved device which assists in guiding a tracheostomy tube towards the incision made in the trachea in order to facilitate proper insertion of the tube.

Another object of the present invention is to provide an obturator which is especially suitable for use with tracheostomy tubes which include a non-constant radius cannula.

A further object of the present invention is to provide an obturator which can be easily inserted and safely removed through straight and curved portions of the non-constant radius cannula.

Another object of the present invention is to provide an obturator which is highly flexible, but able to maintain the geometry of the cannula during the intubation procedure to prevent occlusion, collapse and distortion of the cannula, and to ensure an internal non-disturbed airway.

Still another object of the present invention is to provide an obturator which is highly flexible and will easily assume the preferred contour of the tracheostomy tube, and will maintain the internal geometry of the cannula during intubation.

Another object of the present invention is to provide a multi-component highly flexible obturator made as an integral, single piece member thereby eliminating possible failure of assembly points and enhancing safety of the device.

Still another object of the present invention is to provide a plastic obturator which has a simple structure and is inexpensive to manufacture.

The above and other objects of the present invention are accomplished by a structure of the obturator for use in intubating tracheostomy tubes into a patient's trachea which includes a single-piece, flexible member having a distal end and a proximal end and a shaft means extending therebetween. The shaft means is comprised of a substantially flat strip member and a plurality of segments substantially perpendicular to the flat strip member. The flat strip forms a plurality of hinged portions alternating with the plurality of segments. The flexible member has a grasping means formed at its proximal end and a tip member provided at its distal end. The tip member has a bullet-like conical shape. A smooth transition zone is formed between the tip member and the outer diameter of the tracheostomy tube.

In the preferred embodiment of the present invention, the single-piece, flexible obturator is made of polymeric material and the plurality of segments are dimensioned such as to substantially correspond to the inner diameter of the cannula.

The present invention due to its structure and nature of the material, flexes easily at the hinged portions in the axis of the curved tube portion when it is being inserted or removed from the tracheostomy tube without applying forces which can cause changes in the cannula's shape. At the same time, when placed within the tube, the obturator substantially fills, with the plurality of segments, the interior of the cannula whereby maintaining geometry of the tube during the intubation. This, in turn, prevents occlusion or collapse of the tube during intubation and any distortion of the tube once in place in the patient's trachea, and ensures a non-disturbed airway through the tracheostomy tube device.

The structure of the present invention obturator is substantially resistant to compression forces, which typically in mealable wire-type stylet obturators or strap like plastic current state of the art devices, because they do not fill the cannula completely, allow the obturator tip to push back and complicate the intubating procedure due to the lack of a smooth transition from the obturator tip to the tracheostomy tube outside diameter. The smooth transition is therefore secured between the tip member of the obturator and the outer diameter of the tracheostomy tube device in the present invention structure.

The single-piece obturator structure also increases the reliability of the tracheostomy tube assembly by eliminating additional possible failure points common to all devices of multicomponent configuration, an enhanced safety feature for both the clinician and the patient during intubation procedure.

Additional key features of the preferred embodiment of the present invention include a multi-geometry highly flexible single piece structure and polymeric material construction, resulting in a device that provides easier, more efficient and safer use during the intubation procedure increasing patient safety and comfort.

Other advantages achievable by the present invention will become apparent from the following description of the preferred embodiment of the present invention with reference being made to the accompanying drawings.

DETAILED DESCRIPTION OF THE PREFERRED EMBODIMENT(S)

Figure 1:
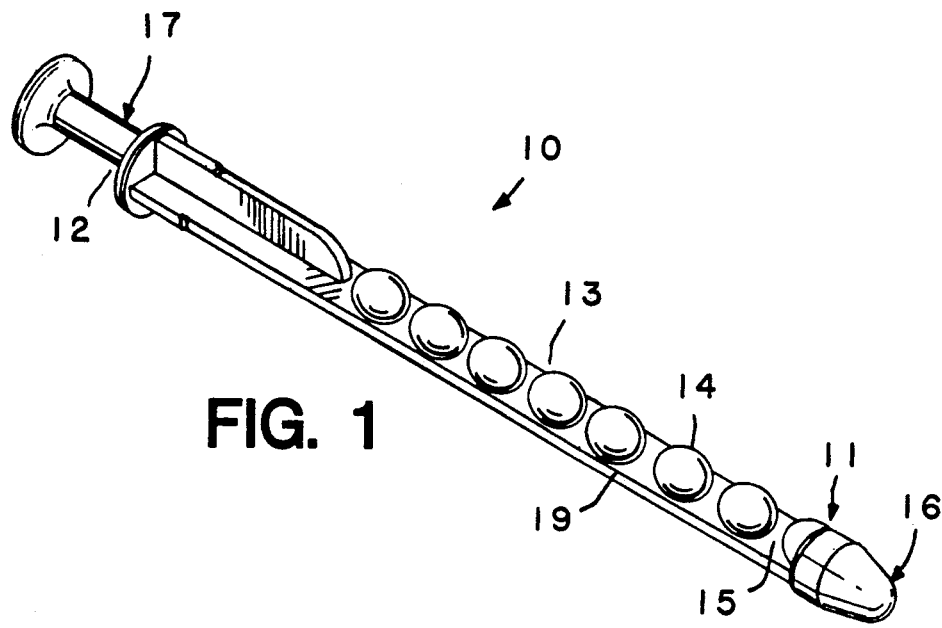
FIG. 1: shows a perspective view of the first preferred embodiment of the present invention obturator.
Figure 2:
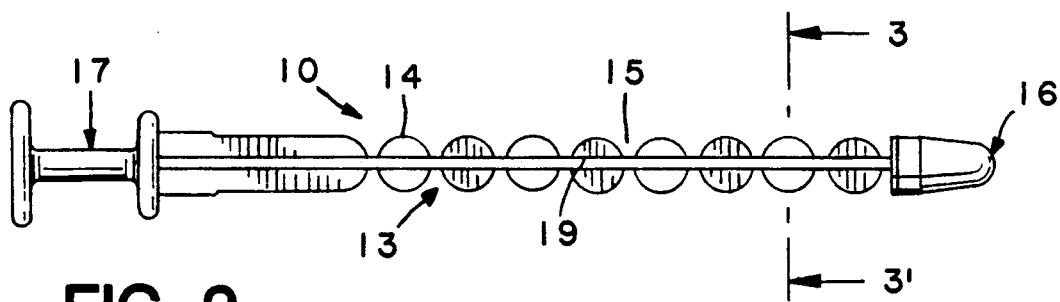
FIG. 2: shows a side view of the embodiment of FIG. 1.
Figure 3:
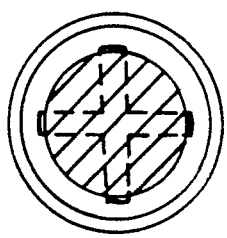
FIG. 3: shows a cross-section of the first embodiment of the present invention obturator taken along lines 3'—3' in FIG. 2.

Referring first to FIGS. 1 and 2, an obturator 10 is shown, which includes a single-piece member having a distal end 11, proximal end 12 and a shaft means 13 extending between the distal and proximal ends 11,12. The shaft means 13 is comprised of a substantially flat member 19 having a rectangular cross-section and having a plurality of segments or protuberances 14 disposed substantially perpendicular to the flat strip member 19. The rectangular cross section of the shaft has a width and thickness with the width substantially exceeding its thickness. This flat strip member 19 forms a plurality of hinged portions 15 alternating with the segments 14. In the preferred embodiment shown in FIGS. 1-4, the segments 14 are bead-like shaped. The obturator 10 includes a grasping means 17 formed at its proximal end 12, and a tip member 16 provided at its distal end 11. In the preferred embodiment, the obturator 10 is made as an integral, plastic, single-piece device.

Figure 4:
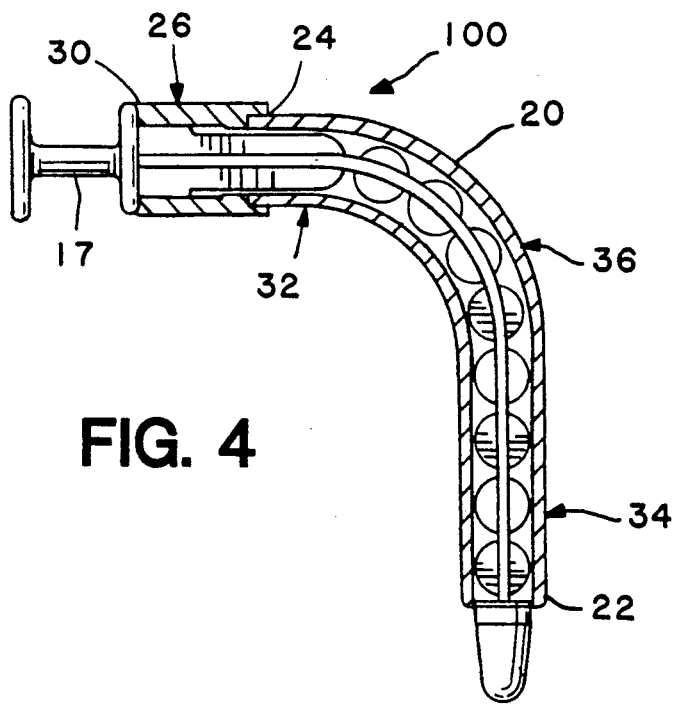
FIG. 4: shows a cross-section view of a non-constant radius tracheostomy tube with the obturator according to the present invention placed inside the tube.

FIG. 4 shows tracheostomy tube 100 including a non-constant radius curved cannula 20 lying substantially with in a give plane and having straight portions 32 and 34 and curved portion 36 located therebetween. The cannula 20 includes a proximal end 24 and a distal end 22. A connector 26 is connected to the proximal end 24 of the straight portion 32. In FIG. 4, the obturator 10 for use in intubating the tracheostomy tube 100 into the patient's trachea is shown in place within the tracheostomy tube 100.

As clearly shown in FIG. 4, the obturator shaft means 13 flexes at the hinged portions 15 in the axis of the curved cannula portion 36. The grasping means 17 forming in the preferred embodiment, a handle projects beyond the end 30 of the connector 26. The tip member 16 of the obturator 10 projects beyond the end 22 of the cannula 20. The tip member 16 has a bullet-like conical shape which facilitates the guiding of the tracheostomy tube during the intubating procedure. As is clearly apparent from FIGS. 3 and 4, the diameters of the plurality of segments 14, substantially corresponds to the inner diameter of the cannula 20. Therefore, when placed within the tube, the obturator substantially spans the interior of the cannula 20 which allows it to maintain the shape of the tube during the intubation.

Such a structure of the obturator is very advantageous, since it substantially prevents occlusion or collapse and distortion of the tracheostomy tube, and ensures the existence of a non-disturbed airway.

Figure 6:
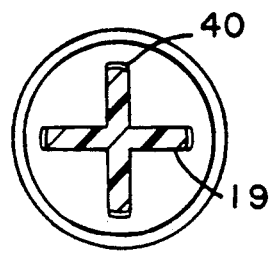
FIG. 6: shows a cross-section view of the embodiment of FIG. 5.
Figure 5:
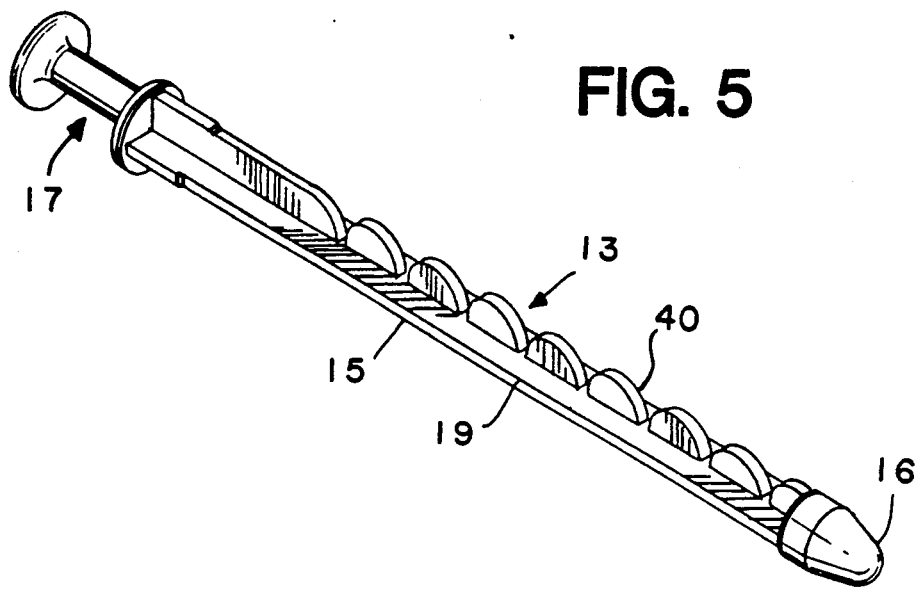
FIG. 5: shows a perspective view of the second preferred embodiment of the present invention obturator.

FIGS. 5 and 6 show another embodiment of the present invention in which the shaft 13 is comprised of a plurality of substantially flat disc-like circular segments 40 which are substantially perpendicular to the hinged portions 15 of the strip member 19. The diameter of circular segments 40 also substantially corresponds to the inner diameter at the cannula 20.

Other shapes for a plurality of segments can be envisioned, for example, having a trapezoidal configuration.

According to the preferred embodiment, the obturator 10 is made of a polymeric material, such as for example polyolefins. However, other plastic materials can be used which are suitable for a multi-hinged geometry.

Due to the multi-hinged structure and the nature of the plastic material, the obturator 10 easily flexes only in the radial direction of the cannula 20 in the axis of the curved tube portion 36, whereby it is easily insertable and removable from the tracheostomy tube 100. These features of the present invention are particularly important and advantageous during the withdrawal of the obturator from the non-constant radius cannula, because the forces necessary for the withdrawal of the obturator from the cannula are substantially decreased.

Also the structure of the present invention obturator with the shaft means including a substantially flat strip member forming hinged portions and a plurality of segments perpendicular to the strip member and alternating with hinged portions, is substantially resistant to compression forces, which typically in mealable wire-type stylets/obturators, allow the obturator tip member to push back towards the inside of the cannula. This, in turn, complicates the intubating procedure due to the lack of a smooth transition between the obturator tip and tracheostomy tube outside diameter.

In the present invention obturator structure, the smooth transition is provided between the tip 16 and the outer diameter of the tracheostomy tube. The multi-component obturator 10 of the present invention is made as an integral single-piece, plastic device. The number of bead-like or circular disc-like segments and hinge portions is selected with respect to the length of the tracheostomy tube and the position of the curved section.

The hinge-like structure allows the obturator to be highly flexible in the axis of the tube curved section. The plurality of segments of the obturator substantially fill up the tube's interior maintaining the integrity of the tracheostomy tube, but at the same time allowing easy flexing during insertion or removal of the obturator from the tracheostomy tube. The obturator's tip is designed with a straight section which absorbs the deflection of the tube and obturator size tolerance without compromising the streamline tip profile. The handle projecting beyond the connector facilitates the withdrawal of the obturator from the tracheostomy tube. It will be understood that variations and modifications may be effected without departing from the spirit and scope of the novel concepts of the present invention.

I claim:

1. In combination, a tracheostomy tube including a curved cannula lying substantially within a given plane and formed with a non-constant radius, and an obturator means insertable into said cannula for guiding intubation of said tracheostomy tube into said cannula, said obturator means comprising:

a single piece member formed of a resilient and flexible material and curvable upon insertion within said cannula with a non-constant radius lying within said given plane, said member having proximal and distal ends and shaft means extending therebetween, said shaft means being of substantially rectangular cross-section having a width and thickness, said width as measured perpendicular to said given plane substantially exceeding its thickness;

said member also having a plurality of protuberances disposed at spaced locations along the length of said shaft means and extending perpendicularly to its width dimension, said shaft means being easily flexible along its length in said given plane of its curvature between said protuberances but being substantially stiff in a direction perpendicular to said given plane because of the greater width of its cross-section; and wherein the insertion and removal of said obturator into said from said tracheostomy tube is easily effected by reason of its easy flexibility in the plane of its curvature while said spaced protuberances aid in maintaining the shape of the tube by preventing collapse, distortion, and occlusion of the tube.

2. An obturator according to claim 1, wherein said protuberances have a bead-like configuration.

3. An obturator according to claim 1, wherein said protuberances are formed as circular discs.

4. An obturator according to claim 1, further comprising a grasping means formed at said proximal end, and a tapered, conical tip member formed at said distal end.

5. An obturator according to claim 1, wherein said shaft means and said protuberances have a maximum dimension at least in said plane, substantially equal to the inner diameter of the cannula.

6. An obturator according to claim 1, wherein said resilient material is polymeric material.

7. An obturator according to claim 5, wherein said protuberances have a bead-like configuration.

8. An obturator according to claim 5, wherein said protuberances are formed as circular discs.

* * * * *